United States Patent [19]

Takematsu et al.

[11] 4,078,913
[45] Mar. 14, 1978

[54] HERBICIDAL 3-(2-PHENYLISOPROPYL)UREA DERIVATIVES

[76] Inventors: Tetsuo Takematsu, Utsunomiya; Shizuo Ohga, Tokyo; Akira Terakawa, Yokohama; Masatomo Ito, Yokohama; Hiroshi Kubo, Yokohama; Nansho Seki, Yokohama, all of Japan

[21] Appl. No.: 597,137

[22] Filed: Jul. 18, 1975

Related U.S. Application Data

[63] Continuation of Ser. No. 314,838, Dec. 13, 1972, abandoned, which is a continuation of Ser. No. 131,789, Apr. 6, 1971, abandoned.

[30] Foreign Application Priority Data

Apr. 8, 1970 Japan .................................. 45-29396
Jul. 17, 1970 Japan .................................. 45-62080

[51] Int. Cl.$^2$ ............................................. A01N 9/20
[52] U.S. Cl. .................................. 71/120; 260/553 A
[58] Field of Search .......................................... 71/120

[56] References Cited

U.S. PATENT DOCUMENTS

3,483,296  12/1969  Martin et al. .......................... 424/322
3,660,484  5/1972  Martin et al. ..........................260/552 R

OTHER PUBLICATIONS

Chemical Abstracts, Index, vol. 51–55, Entries under "Fenvron".

*Primary Examiner*—Lewis Gotts
*Assistant Examiner*—Catherine L. Mills
*Attorney, Agent, or Firm*—Haseltine, Lake & Waters

[57] ABSTRACT

A compound of the general formula

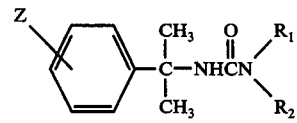

wherein Z is a hydrogen atom or a lower alkyl group; $R_1$ is a hydrogen atom or an alkyl group; and $R_2$ is a lower alkyl group or a phenyl group, which may have one or more lower alkyl, lower alkoxy, nitro, phenyl or trifluoromethyl groups or one or more halogen atoms as benzene substituent is found to be useful as a herbicide selectively combating weeds belonging to barnyardgrass of *Gramineae* and to *Cyperacceae*, without causing any phytotoxicity to rice plants.

22 Claims, No Drawings

HERBICIDAL 3-(2-PHENYLISOPROPYL)UREA DERIVATIVES

This application is a continuation application of Ser. No. 314,838, filed December 13, 1972, which was a continuation application of Ser. No. 131,789, filed April 6, 1971, both now abandoned.

This invention relates to novel 3-(2-phenylisopropyl) urea derivatives having the general formula.

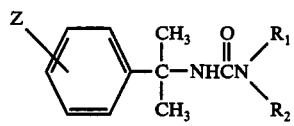

wherein Z is a hydrogen atom or a lower alkyl group; $R_1$ is a hydrogen atom or an alkyl group; and $R_2$ is a lower alkyl group or a phenyl group, which may have one or more lower alkyl, lower alkoxy, nitro, phenyl or trifluoromethyl groups or one or more halogen atoms as benzene substituent. The invention further pertains to herbicidal compositions containing said 3-(2-phenylisopropyl) urea derivatives as active ingredients.

Since the discovery of the herbicidal usage of 1-aryl-3,3-dialkylureas, e.g. fenuron, monuron, and diuron, in the U.S.A. in 1951, many researchers have continued to prepare and test a variety of urea derivatives with the hope of finding better herbicides. Generally herbicides having a urea structure are phytotoxicants having no substantial selectivity and may cause injury to major crops. For this reason the urea herbicides are used only for indiscriminative control of weed in non-cultivated lands or orchard fields.

We have found that 3-(2-phenylisopropyl) urea derivatives of the aforesaid general formula have no phytotoxicity to rice plants belonging to the Gramineae genus of the grass family which is one of major crops, but show extremely strong phytotoxicity against weeds belonging to the barnyardgrass of *Gramineae* and to *Cyperaceae*.

Conventional urea type herbicides, e.g. fenuron, monuron, diuron, and neburon, generally cause injury to paddy rice plants, when the herbicides are used at the concentration capable of killing barnyardgrass. While the herbicidal compositions according to the present invention are perfectly specific in such substantial selectivity that they can control a wide scope of weeds belonging to barnyard-grass or Cyperus without giving any phytotoxicity to paddy rice.

Weeds belonging to Cyperus as well as those belonging to barnyardgrass are quite serious for farmers since they contaminate rice fields. However, the herbicidal compositions of the present invention can exterminate these weeds and can inhibit the germination thereof for a long period of time. Further, the herbicidal compositions of the present invention have prominent herbicidal effects on such paddy field weeds as monochoria, waterwort, waterstarwort, toothcup and such upland weeds as crabgrass and sedge.

Most of the 3-(2-phenylisopropyl)urea derivatives themselves, which are to the active ingredient compounds of the herbicidal compositions according to the present invention, are novel compounds, and can be prepared according to such procedures as represented by the following reaction scheme:

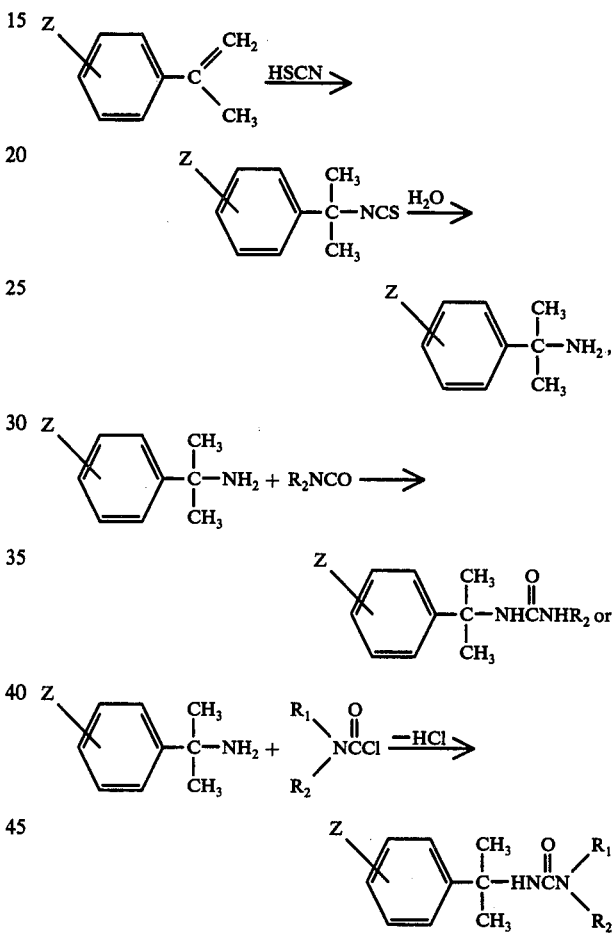

wherein Z, $R_1$ and $R_2$ are as defined above.

Typical examples of active ingredient compounds of the present herbicidal compositions are as shown below.

| Compound No. | Name | Structural formula | m.p. (° C.) |
|---|---|---|---|
| 1 | 3-(2-Phenylisopropyl)-1-phenylurea | | 183–186 |
| 2 | 3-(2-Phenylisopropyl)-1-(2-chlorophenyl)urea | | 171–176 |

-continued

| Compound No. | Name | Structural formula | m.p. (° C.) |
|---|---|---|---|
| 3 | 3-(2-Phenylisopropyl)-1-(3-chlorophenyl)urea | C₆H₅-C(CH₃)₂-NHCONH-C₆H₄-Cl (3-Cl) | 170–173 |
| 4 | 3-(2-Phenylisopropyl)-1-(4-chlorophenyl)urea | C₆H₅-C(CH₃)₂-NHCONH-C₆H₄-Cl (4-Cl) | 220–222 |
| 5 | 3-(2-Phenylisopropyl)-1-methylurea | C₆H₅-C(CH₃)₂-NHCONHCH₃ | 145–149 |
| 6 | 3-(2-Phenylisopropyl)-1,1-dimethylurea | C₆H₅-C(CH₃)₂-NHCON(CH₃)₂ | 124–127 |
| 7 | 3-(2-Phenylisopropyl)-1-o-tolylurea | C₆H₅-C(CH₃)₂-NHCONH-C₆H₄-CH₃ (o) | 173 |
| 8 | 3-(2-Phenylisopropyl)-1-m-tolylurea | C₆H₅-C(CH₃)₂-NHCONH-C₆H₄-CH₃ (m) | 165.5 |
| 9 | 3-(2-Phenylisopropyl)-1-p-tolylurea | C₆H₅-C(CH₃)₂-NHCONH-C₆H₄-CH₃ (p) | 201–205 |
| 10 | 3-(2-Phenylisopropyl)-1-2,4-xylylurea | C₆H₅-C(CH₃)₂-NHCONH-C₆H₃(CH₃)₂ (2,4) | 163 |
| 11 | 3-(2-Phenylisopropyl)-1-(2-methoxyphenyl)urea | C₆H₅-C(CH₃)₂-NHCONH-C₆H₄-OCH₃ (2) | 183.5 |
| 12 | 3-(2-Phenylisopropyl)-1-(3-methoxyphenyl)urea | C₆H₅-C(CH₃)₂-NHCONH-C₆H₄-OCH₃ (3) | 164–165 |
| 13 | 3-(2-Phenylisopropyl)-1-(4-methoxyphenyl)urea | C₆H₅-C(CH₃)₂-NHCONH-C₆H₄-OCH₃ (4) | 175–176 |
| 14 | 3-(2-Phenylisopropyl)-1-(4-isopropylphenyl)urea | C₆H₅-C(CH₃)₂-NHCONH-C₆H₄-CH(CH₃)₂ | 175–177 |
| 15 | 3-(2-Phenylisopropyl)-1-(4-ethylphenyl)urea | C₆H₅-C(CH₃)₂-NHCONH-C₆H₄-C₂H₅ | 177.5–178 |

-continued

| Compound No. | Name | Structural formula | m.p. (° C.) |
|---|---|---|---|
| 16 | 3-(2-Phenylisopropyl)-1-m-nitrophenylurea | Ph-C(CH₃)₂-NHCONH-(m-NO₂-C₆H₄) | 176.5 |
| 17 | 3-(2-Phenylisopropyl)-1-(3-trifluoromethylphenyl)-urea | Ph-C(CH₃)₂-NHCONH-(m-CF₃-C₆H₄) | 149.5–150 |
| 18 | 3-(2-Phenylisopropyl)-1-p-diphenylurea | Ph-C(CH₃)₂-NHCONH-(p-C₆H₅-C₆H₄) | 153–153.5 |
| 19 | 3-(2-Phenylisopropyl)-1-(3-chloro-o-tolyl)urea | Ph-C(CH₃)₂-NHCONH-(2-CH₃-3-Cl-C₆H₃) | 186.5–187 |
| 20 | 3-(2-Phenylisopropyl)-1-(3,4-dichlorophenyl)urea | Ph-C(CH₃)₂-NHCONH-(3,4-Cl₂-C₆H₃) | 180–182 |
| 21 | 3-(2-p-Tolylisopropyl)-1-phenylurea | (p-CH₃-C₆H₄)-C(CH₃)₂-NH-CO-NH-C₆H₅ | 193.5–194 |
| 22 | 3-(2-p-Tolylisopropyl)-1-m-tolylurea | (p-CH₃-C₆H₄)-C(CH₃)₂-NH-CO-NH-(m-CH₃-C₆H₄) | 164.5–164.5 |
| 23 | 3-(2-p-Tolylisopropyl)-1-p-tolylurea | (p-CH₃-C₆H₄)-C(CH₃)₂-NH-CO-NH-(p-CH₃-C₆H₄) | 206–207.5 |
| 24 | 3-(2-p-Tolylisopropyl)-1-(2,3-dimethylphenyl)urea | (p-CH₃-C₆H₄)-C(CH₃)₂-NH-CO-NH-(2,3-(CH₃)₂-C₆H₃) | 209–209.5 |
| 25 | 3-(2-p-Tolylisopropyl)-1-(2,4-dimethylphenyl)urea | (p-CH₃-C₆H₄)-C(CH₃)₂-NH-CO-NH-(2,4-(CH₃)₂-C₆H₃) | 219–220 |
| 26 | 3-(2-p-Tolylisopropyl)-1-(2,5-dimethylphenyl)urea | (p-CH₃-C₆H₄)-C(CH₃)₂-NH-CO-NH-(2,5-(CH₃)₂-C₆H₃) | 209.5–210.5 |
| 27 | 3-(2-p-Tolylisopropyl)-1-(3,4-dimethylphenyl)urea | (p-CH₃-C₆H₄)-C(CH₃)₂-NH-CO-NH-(3,4-(CH₃)₂-C₆H₃) | 187–188.5 |
| 28 | 3-(2-m-Tolylisopropyl)-1-phenylurea | (m-CH₃-C₆H₄)-C(CH₃)₂-NH-CO-NH-C₆H₅ | 198–198.5 |

-continued

| Compound No. | Name | Structural formula | m.p. (° C.) |
|---|---|---|---|
| 29 | 3-(2-m-Tolylisopropyl)-1-p-tolylurea | | 204–205 |
| 30 | 3-(2-m-Tolylisopropyl)-1-m-tolylurea | | 152–155 |
| 31 | 3-(2-m-Tolylisopropyl)-1-2,3-dimethylphenyl)urea | | 170.5–171.5 |
| 32 | 3-(2-m-Tolylisopropyl)-1-2,4-dimethylphenyl)urea | | 181–182 |
| 33 | 3-(2-m-Tolylisopropyl)-1-2,5-dimethylphenyl)urea | | 193.5–194.5 |
| 34 | 3-(2-m-Tolylisopropyl)-1-3,4-dimethylphenyl)urea | | 199–200 |
| 35 | 3-(2-o-Tolylisopropyl)-1-phenylurea | | 198.5–199 |
| 36 | 3-(2-o-Tolylisopropyl)-1-p-tolylurea | | 185.5–186.5 |
| 37 | 3-(2-o-Tolylisopropyl)-1-m-tolylurea | | 151.5–152.5 |
| 38 | 3-(2-o-Tolylisopropyl)-1-(2,3-dimethylphenyl)urea | | 187–188 |
| 39 | 3-(2-o-Tolylisopropyl)-1-(2,4-dimethylphenyl)urea | | 197.5–198.5 |
| 40 | 3-(2-o-Tolylisopropyl)-1-(2,5-dimethylphenyl)urea | | 220–221 |

| Compound No. | Name | Structural formula | m.p. (° C.) |
| --- | --- | --- | --- |
| 31 | 3-(2-o-Tolylisopropyl)-1-(3,4-dimethylphenyl)urea | $\text{(o-CH}_3\text{-C}_6\text{H}_4\text{)C(CH}_3\text{)}_2\text{-NH-C(=O)-NH-(3,4-(CH}_3\text{)}_2\text{-C}_6\text{H}_3\text{)}$ | 194–195.5 |

The active ingredient compounds of the aforesaid general formula are practically usable by formulating them into various forms. That is, the compounds may be formulated into any of such known forms as dusts, granules, emulsifiable concentrates, wettable powders, pastes, etc. by use of inert solid carriers such as clay, kaolin, diatomaceous earth, calcium silicate and talc, liquid media such as water, methanol, benzene and toluene, or wetting agents, dispersants, emulsifiers, etc. Further, the herbicidal compositions of the present invention may be used together with or in admixture with fertilizers, soil improvers, insecticides, fungicides, other herbicides or plant growth regulators.

Procedures for preparation of the present herbicidal compositions are illustrated below with reference to examples.

EXAMPLE 1

A mixture comprising 50 parts by weight of 3-(2-phenylisopropyl)-1-phenylurea, 45 parts by weight of bentonite and 5 parts by weight of polyoxyethylene alkylaryl ether is thoroughly pulverized to obtain a wettable powder containing 50% of the said active ingredient compound.

EXAMPLE 2

A mixture comprising 10 parts by weight of 3-(2-phenylisopropyl)-1-(3-chlorophenyl)urea, 50 parts by weight of bentonite, 40 parts by weight of talc and a small amount of sodium alkylbenzenesulfonate is thoroughly kneaded with water, granulated and then dried to obtain a granule of 20 to 100 mesh.

EXAMPLE 3

A mixture comprising 50 parts by weight of 3-(2-phenylisopropyl)-1-m-tolylurea, 45 parts by weight of bentonite and 5 parts by weight polyoxyethylene alkylaryl ether is thoroughly pulverized to obtain a wettable powder containing 50% of the said active ingredient compound.

EXAMPLE 4

A mixture comprising 10 parts by weight of 3-(2-phenylisopropyl)-1-(m-tolyl-fluoromethylphenyl)urea, 15 parts by weight of bentonite, 73 parts by weight of clay and 2 parts by weight of sodium dodecylbenzenesulfonate is thoroughly kneaded with about 25 parts by weight of water, granulated and then dried to obtain a granule containing 10% of the said active ingredient compound.

EXAMPLE 6

A mixture comprising 50 parts by weight of 3-(2-m-tolylisopropyl)-1-p-tolylurea, 45 parts by weight of bentonite and 5 parts by weight of polyoxyethylene alkylaryl ether is thoroughly pulverized to obtain a wettable powder containing 50% of the said active ingredient compound.

EXAMPLE 7

A mixture comprising 10 parts by weight of 3-(2-m-tolylisopropyl)-1-(2,4-dimethylphenyl)urea, 15 parts by weight of bentonite, 73 parts by weight of clay and 2 parts by weight of sodium alkylbenzenesulfonate is thoroughly kneaded with about 25 parts by weight of water, granulated and then dried to obtain a granule containing 10% of the said active ingredient compound.

Effects of the present herbicidal compositions are explained below with reference to test examples.

TEST EXAMPLE 1

Ceramic pots of 10/20000 ares were packed with diluvium volcanic ash soil and watered to make paddy conditions. Four sheaves of rice seedlings and slender spikerush were transplanted into each pot, and water was charged to the depth of 3 cm. Subsequently seeds of barnyardgrass were sown into the paddy soil. After two days a given amount of the test chemicals was applied, and 30 days thereafter the herbicidal effects of the chemicals and the influence on the paddy rice were evaluated. The results obtained were as set forth in Table 1, in which the compounds of the present invention are represented by the numbers of the previously exemplified compounds (the same shall apply hereinafter).

Table 1

| Test compound No. | Amount (g/10 ares) | Herbicidal effect (%) barnyardgrass | Herbicidal effect (%) slender spikerush | Phytotoxicity to paddy rice |
| --- | --- | --- | --- | --- |
| (1) | 400 | 100 | 100 | None |
|  | 200 | 100 | 100 | None |
|  | 100 | 87 | 82 | None |
| (2) | 400 | 100 | 100 | None |
|  | 200 | 98 | 95 | None |
|  | 100 | 75 | 84 | None |
| (3) | 400 | 85 | 81 | None |
|  | 200 | 37 | 72 | None |
|  | 100 | 14 | 34 | None |
| (5) | 400 | 82 | 20 | None |
|  | 200 | 34 | 11 | None |
|  | 100 | 18 | 0 | None |
| (6) | 400 | 98 | 65 | None |
|  | 200 | 81 | 46 | None |
|  | 100 | 58 | 15 | None |
| 3-(3,4-Dichlorophenyl)-1,2-dimethylurea (Control) | 400 | 100 | 21 | 100 |
|  | 200 | 87 | 9 | 83 |
|  | 100 | 64 | 0 | 57 |

In Table 1, the herbicidal activity and the phytotoxicity to paddy rice plants are individually represented by weight % of the raw plants compared with non-treated plot, assuming as 100, respectively, the herbicidal activity of a chemical which could kill all the weeds, and the extent of phytotoxicity in areas where the rice plants were completely killed.

TEST EXAMPLE 2

Seeds of crabgrass, umbrella sedge, upland rice and soy bean were sown in diluvium volcanic ash field, which had been divided into sections of 1.5 m² in area.

Subsequently, each of aqueous suspensions of wettable powders containing 50% of the active ingredients shown in Table 2 was applied to the field at the dosage of 1,000 g. per 10 ares, and 24 days thereafter, the germination-inhibiting and killing ratio (%) of the chemicals were observed. The results obtained were as set forth in Table 2.

Table 2

| Test compound | Crabgrass | Umbrella sedge | Upland rice | Soy bean |
|---|---|---|---|---|
| (1) | 87 | 91 | 0 | 11 |
| (2) | 79 | 76 | 0 | 5 |
| (3) | 51 | 42 | 0 | 0 |
| (4) | 21 | 17 | 0 | 0 |
| (5) | 80 | 75 | 0 | 0 |
| (6) | 82 | 63 | 0 | 0 |

TEST EXAMPLE 3

A given amount of each of the test chemicals shown in Table 3 was applied to soil, and then 20 mm. of artificial rain was applied thereto for 24 hours. Thereafter, the soil was recovered at portions of each 1 cm. in depth from the surface, and the amount of leached chemical was examined by measuring the root extension inhibitory ratio of barnyardgrass according to the following equation:

$$\text{Root extension inhibitory ratio} = 100 - \left( \frac{\text{Root length in treated area}}{\text{Root length in control area}} \times 100 \right)$$

The results obtained were as set forth in Table 3.

Table 3

| Compound No. | Amount (g/10 ares) | Depth of soil (cm) | Root extension inhibitory ratio |
|---|---|---|---|
| (1) | 500 | 0 - 1 | 91.2 |
|  |  | 1 - 2 | 12.0 |
|  |  | 2 - 3 | 0 |
| (2) | 500 | 0 - 1 | 87.5 |
|  |  | 1 - 2 | 91 8.0 |
|  |  | 2 - 3 | 0 |
| PCP (Control chemical) | 1,000 | 0 - 1 | 90.5 |
|  |  | 1 - 2 | 17.1 |
|  |  | 2 - 3 | 7.0 |
|  |  | 3 - 4 | 0 |

TEST EXAMPLE 4

Ceramic pots of 1/2000 are were packed with diluvium volcanic ash soil and watered to make paddy conditions. Three sheaves of rice seedlings and two sheaves of slender spikerush were transplanted into each pot. Subsequently seeds of barnyardgrass were sown into the paddy soil 1 cm. beneath the surface, and the pots were irrigated to the depth of 3 cm. After two days 50 g. per 1 are of the test chemicals were applied to the irrigation water in the form of wettable powders. The herbicidal effectiveness of the chemicals and the influence on the paddy rice were investigated after three weeks.

The evaluation of herbicidal effects was carried out by measuring the weights of survival weeds in treated areas and evaluating the measured weights in terms of growth inhibition ratios according to the following indexes:

| Herbicidal effect | Index |
|---|---|
| Complete killing | 5 |
| 80–99% Inhibition | 4 |
| 60–79% Inhibition | 3 |
| 40–49% Inhibition | 2 |
| 20–39% Inhibition | 1 |
| No inhibition | 0 |

The results obtained were as set forth in Table 4. For comparison, 3-(3,4-dichlorophenyl)-1,1-dimethylurea was used as a control chemical.

Table 4

| Compound No. | Herbicidal effect barnyardgrass 250 g/10 ares | 500 g/10 ares | slender spiderush 250 g/10 ares | 500 g/10 ares | Phytotoxicity to paddy rice plants |
|---|---|---|---|---|---|
| (7) | — | 5 | — | 4–5 | None |
| (8) | — | 5 | — | 5 | None |
| (9) | — | 5 | — | 5 | None |
| (10) | — | 5 | — | 5 | None |
| (11) | — | 4 | — | 4 | None |
| (12) | — | 5 | — | 5 | None |
| (13) | — | 5 | — | 5 | None |
| (14) | — | 5 | — | 4–5 | None |
| (15) | — | 5 | — | 4–5 | None |
| (16) | — | 4–5 | — | 4 | None |
| (17) | — | 5 | — | 5 | None |
| (18) | — | 3–4 | — | 4–5 | None |
| (19) | — | 5 | — | 5 | None |
| (20) | — | 4 | — | 4 | None |
| (21) | 5 | 5 | 4–5 | 5 | None |
| (22) | 2 | 4 | 3 | 3 | None |
| (23) | 4 | 4–5 | 3 | 4–5 | None |
| (29) | 4 | 5 | 4 | 4 | None |
| (30) | 4 | 5 | 5 | 5 | None |
| (32) | 5 | 5 | 4 | 4 | None |
| (35) | 1 | 4 | 4 | 4 | None |
| (36) | 4 | 5 | 4 | 5 | None |
| (38) | 5 | 5 | 2 | 2 | None |
| (39) | 5 | 5 | 4 | 5 | None |
| Control chemical | 4–5 | 5 | 1 | 3–4 | Marked |

The preparation, formulations and particle size of the wettable powders, aqueous suspensions, dusts, granules, emulsifiable concentrates and solutions in solvents are well known to those skilled in the art. The active ingredient is usually present in the herbicidal compositions in a range of about 5 to 50 parts by weight per 100 parts by weight of wettable powder and emulsifiable formulations; 5 to 20 parts by weight per 100 parts by weight of granule oil formulations; and 1 to 10 parts by weight of dust formulations. Formulations containing other than the above quantities of active ingredient can easily be prepared by those skilled in the art. Application of the herbicidal compositions of this invention to the soil and/or plant is well known to those skilled in the art and may be by applying to the surface of the soil or by employing a liquid carrier to accomplish the penetration and impregnation. The application of herbicidal formulations to the surface of soil or to above ground portions of plants can be carried out by conventional methods, e.g., power dusters, boom and hand sprayers and spray dusters. Suitable amount for the application may be within the range of 10 to 100 grams of an active ingredient per are.

While the illustrative embodiments of the invention have been described hereinbefore, it will be understood that various other modifications will be apparent to and can readily be made by those skilled in the art without departing from the scope and spirit of the invention.

What we claim is:

1. A method for killing weeds growing in a field which comprises applying to the field a herbicidally effective amount of a compound of the formula

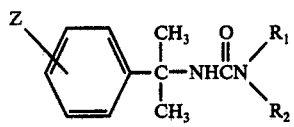

wherein Z is a hydrogen atom or a lower alkyl group, $R_1$ is a hydrogen atom or a lower alkyl group, and $R_2$ is a phenyl group which may have one or more lower alkyl, lower alkoxy, nitro, phenyl or trifluoromethyl groups or one or more halogen atoms as benzene substituent.

2. The method of claim 1 wherein the weeds are those of *Gramineae* and *Cyperaceae* families.

3. The method of claim 1 wherein the weeds are growing in a rice field, with the rice plants being free from any phytotoxicity thereagainst.

4. The method of claim 1 wherein the weeds are growing in non-rice fields of useful plants with said useful plants being free from any phytotoxicity thereagainst.

5. The method of claim 1 wherein the compound is 3-(2-phenylisopropyl)-1-phenyl urea.

6. The method of claim 1 wherein the compound is 3-(2-phenylisopropyl)-1-(4-methylphenyl) urea.

7. The method of claim 1 wherein the compound is 3-(2-phenylisopropyl)-1-(2,4-dimethylphenyl) urea.

8. The method of claim 1 wherein the compound is applied as a composition in combination with an inert carrier, the amount of said compound being 5 to 50% by weight of the composition.

9. The method of claim 3 wherein the weed is slender spikerush.

10. The method of claim 3 wherein the weed is barnyardgrass.

11. The method of claim 1 wherein the compound is used at the dosage of 10–100 g/are of the field.

12. The method of claim 2 wherein the compound is 3-(2-phenylisopropyl)-1-phenyl urea.

13. The method of claim 2 wherein the compound is 3-(2-phenylisopropyl)-1-(4-methylphenyl) urea.

14. The method of claim 2 wherein the compound is 3-(2-phenylisopropyl)-1-(2,4-dimethylphenyl) urea.

15. The method of claim 9 wherein the compound is 3-(2-phenylisopropyl)-1-phenyl urea.

16. The method of claim 9 wherein the compound is 3-(2-phenylisopropyl)-1-(4-methylphenyl) urea.

17. The method of claim 9 wherein the compound is 3-(2-phenylisopropyl)-1-(2,4-dimethylphenyl) urea.

18. The method of claim 10 wherein the compound is 3-(2-phenylisopropyl)-1-phenyl urea.

19. The method of claim 10 wherein the compound is 3-(2-phenylisopropyl)-1-(4-methylphenyl) urea.

20. The method of claim 10 wherein the compound is 3-(2-phenylisopropyl)-1-(2,4-dimethylphenyl) urea.

21. The method of claim 4 wherein the weed is barnyard grass or crabgrass.

22. The method of claim 4 wherein the weed is slender spikerush or embrella sedge.

* * * * *